US 7,297,727 B2
Nov. 20, 2007

(12) United States Patent
Aubart et al.

(54) TRIARYLSILYL(METH)ACRYLOYL-CONTAINING POLYMERS FOR MARINE COATING COMPOSITIONS

(75) Inventors: Mark Anthony Aubart, Malvern, PA (US); Michael Benjamin Abrams, Philadelphia, PA (US); Gary Stephen Silverman, Chadds Ford, PA (US); Jerome Obiols, Lyons (FR); Kenneth Kuo-Shu Tseng, Lawrenceville, PA (US); David A. Mountz, King of Prussia, PA (US)

(73) Assignee: Arkema Inc., Philadelphia, PA (US)

( * ) Notice: Subject to any disclaimer, the term of this patent is extended or adjusted under 35 U.S.C. 154(b) by 138 days.

(21) Appl. No.: 10/705,693

(22) Filed: Nov. 10, 2003

(65) Prior Publication Data

US 2004/0138332 A1    Jul. 15, 2004

Related U.S. Application Data (63) Continuation-in-part of application No. 10/442,461, filed on May 21, 2003, now abandoned.

(60) Provisional application No. 60/383,961, filed on May 30, 2002.

(51) Int. Cl.
*C09D 5/16* (2006.01)

(52) U.S. Cl. .................. 523/122; 523/177; 525/479

(58) Field of Classification Search .............. 523/122, 523/177; 525/479
See application file for complete search history.

(56) References Cited

U.S. PATENT DOCUMENTS

| 4,593,055 A | 6/1986 | Gitlitz et al. ............... 523/122 |
| 4,594,365 A | 6/1986 | Russell et al. .............. 523/122 |
| 4,687,792 A | 8/1987 | Russell et al. |
| 4,957,989 A | 9/1990 | Saitoh |
| 5,436,284 A | 7/1995 | Honda et al. ............... 523/122 |
| 5,795,374 A | 8/1998 | Itoh et al. ..................... 106/16 |

FOREIGN PATENT DOCUMENTS

| EP | 0646630 | 4/1997 |
| EP | 0775733 | 5/1997 |
| EP | 0714957 | 3/1998 |
| EP | 1016681 A2 | 7/2000 |
| EP | 0802243 | 6/2001 |
| EP | 1 127 902 A1 | 8/2001 |
| EP | 1127925 A | 8/2001 |
| JP | 8-269389 A | 10/1996 |
| JP | 11-335619 | 12/1999 |
| JP | 11335619 | 12/1999 |
| WO | WO 84/02915 | 8/1984 |
| WO | WO 91/14743 | 10/1991 |
| WO | WO 00/77102 A1 | 12/2000 |

*Primary Examiner*—Kriellion A Sanders
(74) *Attorney, Agent, or Firm*—Thomas F. Roland (57) ABSTRACT

Polymers containing triarylsilyl(meth)acryloyl units are erodible in seawater and can be used to formulate antifouling marine paints. The polymers are characterized by low levels of triarylsilyl(meth) acrylate units and an erosion rate in seawater of 2 to about 15 microns per month.

19 Claims, 3 Drawing Sheets

TRIARYLSILYL(METH)ACRYLOYL-CONTAINING POLYMERS FOR MARINE COATING COMPOSITIONS

This application claims priority of U.S. Provisional Application 60/383,961 filed May 30, 2002. This application is a continuation in part of U.S. patent application Ser. No. 10/442,461, filed May 21, 2003 now abandoned.

FIELD OF THE INVENTION

This invention relates to polymers for self-polishing marine antifouling paints. More particularly, the invention relates to polymer binders, which provide an erosion rate in seawater that is suitable for use in marine antifouling paints. These polymer binders contain pendant triarylsilyl(meth)acryloyl group at lower levels than previously believed necessary to achieve an erosion rate in seawater that is suitable for use in marine antifouling paints. The polymers are characterized by an erosion rate in seawater of about 2 to about 15 microns/month.

BACKGROUND OF THE INVENTION

The polymers widely used at present to fabricate self-polishing marine antifouling paints are polymers that contain pendant organotin ester (e.g., acrylate) groups. Indeed, marine antifouling paints based on organotin acrylate polymers have dominated the market for over 20 years. The organotin acrylate-containing polymers, when formulated into a paint and applied to the bottom (i.e., hull) of a marine vessel, hydrolyze in seawater to release an organotin compound (usually tributyltin oxide) that is an active antifoulant preventing marine plants and other organisms from adhering to the vessel bottom. This fouling (i.e., undesirable attachment of organisms to a marine surface) results in increased drag which can significantly increase fuel consumption and, therefore, operating costs. In addition, movement of the vessel through water erodes the paint surface to constantly expose a fresh polymer surface to the hydrolytic effect of seawater. This constant erosion of the paint surface results in the development and maintenance of a smooth surface on the immersed exterior of the marine vessel, which also contributes to reduced drag and greater efficiency.

Further, these paints, properly formulated and applied, have the ability to remain effective for 5 years. This is important because large vessels (e.g., oil tankers and container ships) are dry-docked at 5-year intervals for routine maintenance and inspection; it is most convenient to repaint the hull exterior during these periodic maintenance episodes.

Although effective, the use of organotin-containing polymers in antifouling marine paints has come under attack due to the adverse effect that organotin compounds are believed to have upon the marine environment. The U.S. Environmental Protection Agency (EPA) has significantly restricted the continued use of organotin compounds and the Marine Environmental Protection Committee (MEPC) of the International Maritime Organization (IMO), a unit of the United Nations, has recently approved a resolution to phase out and eventually prohibit the use of organotin-containing materials in antifouling paints.

As a result, there is a need in the art for improved erodible antifouling paint compositions comprising film-forming polymers that are free of tin, while retaining the good antifouling and self-polishing properties as well as the longevity of the organotin-containing antifouling paints.

U.S. Pat. No. 4,593,055 discloses that silylacrylate copolymers of formula where X is H or $CH_3$ R is selected from the group consisting of —$SiR'_n R''_{3-n}$ or —$Si(OR'_n R''_{3-n})_3$
wherein R' and R" are independently straight or branched chain alkyl $C_1$-$C_{10}$ or phenyl and n=0-3 are useful to formulate marine antifoulant coatings. The organosilylacrylate component is present in the Examples in amounts ranging from 20 to 40 mole percent.

U.S. Pat. No. 5,436,284 discloses that copolymers containing silylacrylate units are useful to formulate marine antifoulant coating compositions. The Examples (Monomer A4 in Table 3) show arylsilylacrylate copolymers containing 45 and 50 percent by weight of arylsilylacrylate component.

EP 1 127 925 A1 discloses polymeric binders for marine antifoulant paints that contain triarylsilylacrylate groups. The patent teaches that the polymer contains from 20 to 70 percent by weight of triarylsilyl(meth)acrylate, preferably from 30 to 65 percent by weight, and more preferably from 50 to 60 percent by weight.

U.S. Pat. No. 5,795,374 discloses marine antifoulant paints formulated from polymers containing triorganosilyl groups; Monomer M4 is diphenyl-t-butylsilyl acrylate, which is employed in an amount of 10 wt % to make polymer S4. This weight represents about 3 mole %, which, as will be seen from the data, is too low for proper erosion of the polymer film.

U.S. Pat. No. 4,593,055 discloses that marine antifouling paints can be formulated from copolymers containing a hydrolysable triorganosilyl residue, including an arylsilyl residue. The preferred level of triorganosilyl acrylate or methacrylate in the copolymer is from 25 to 40 mole percent.

WO91/14743 discloses erodible marine antifoulant paints with polymeric binders having organosilyl functional groups with the paint having increased storage stability when containing antifouling agents containing copper or zinc. Increased paint storage stability is obtained by using monoamine and quaternary ammonium compounds which inhibit gelation associated with such binders and copper or zinc containing antifouling agents.

Additional patents that concern triorganosilyl containing polymers as binders for marine antifouling paints are: JP 63-057676 which discloses adding a polymethyl silsesquioxane powder for stability when the paint has copper containing antifoulant compounds; EP 714957 B1 which discloses a copolymer containing a triorganosilylacrylate and as an essential ingredient a monomer containing an acryloyloxy, a methacryloyloxy, maleinoyloxy or fumaroyloxy group; EP 0802243 B1 which discloses a marine antifouling paint having an organosilylacrylate based polymeric binder and a rosin compound to improve the erosion rate of the paint;

The following listed patents and applications further disclose terpolymers comprising triorganosily(meth) acryloyl pendant groups useful as binders in marine antifouling coatings: EP 0646630B1, EP 0775733A1, EP 1016681A2, EP 1127925A1, JP 8-269389A, U.S. Pat. No. 4,594,365, U.S. Pat. No. 5,436,284, U.S. Pat. No. 5,795,374, WO 84/02915, WO 91/14743, WO 0077102A1.

SUMMARY OF THE INVENTION

The present invention relates to the discovery that triarylsilyl(meth)acrylate-containing polymers, where the triarylsilyl(meth)acrylate component is present at surprisingly low levels, are useful to produce marine antifouling paints that have self polishing properties.

In one aspect, the invention relates to seawater-erodible polymers comprising the residue of triarylsilyl(meth)acrylate monomer and the residue of two or more ethylenically unsaturated monomers copolymerizable with said triarylsilyl(meth)acrylate monomer, said polymer characterized by an erosion rate in seawater of 2 to 15 microns/month.

As used herein, -the term "copolymer" includes polymers comprising two or more different monomeric units, e.g. polymers containing three different monomeric units, also known as terpolymers. Also, in practicing the present invention, mixtures of polymers may be used in antifouling paint compositions with the proviso that the total of the triarylsilyl (meth)acrylate is greater than 9 mole percent and less than 20 mole percent for the mixture of polymers even though each individual polymer may be outside the mole percent range of greater than 9 mole percent and less than 20 mole percent.

In another embodiment, the present invention relates to a self-polishing antifouling marine coating which comprises a triarylsilyl(meth)acrylate-containing polymer and a toxicant, the triarylsilyl(meth)acrylate-containing polymer containing from above 9 to about 20 mole percent of triarylsilyl (meth)acryloyl component and characterized by an erosion rate in seawater of from about 2 to about 15 microns/month.

In another embodiment, the invention relates to triarylsilyl(meth)acrylate-containing polymers wherein the mole percentage of the triarylsilyl(meth)acryloyl component is in the range of from above 9 to about 20 mole percent.

In one aspect, the invention relates to a seawater-erodible polymer comprising randomly recurring units of formula where A represents from above 9 to about 20 mole percent of the polymer and comprises one or more triarylsilyl(meth) acrylate and B represents the residue of two or more ethylenically unsaturated monomers copolyinerizable with A, said polymer characterized by an erosion rate in seawater of from 2 to about 15 microns/month.

In another aspect, the invention relates to a self-polishing antifouling marine coating composition comprising a triarylsilyl(meth)acrylate-containing polymer and a toxicant, the triarylsilyl(meth)acrylate-containing polymer characterized by an erosion rate in seawater of from about 2 to about 15 microns/month and comprising randomly recurring units of formula where A is present in an amount of from above 9 to about 20 mole percent and comprises triarylsilyl(meth) acrylate, and B is the residue of two or more ethylenically unsaturated monomers copolymerizable with A.

The polymers of the present invention are prepared by polymerizing triarylsilyl(meth)acrylate with two or more ethylenically unsaturated monomers which are polymerizable therewith. As used herein the term "triarylsilyl(meth) acrylate" is intended to encompass both triarylsilylacrylate and triarylsilylmethacrylate; the same is the case when "triarylsilyl (meth)acryloyl" is used.

The term "aryl" as used here includes substituted and unsubstituted aryl and heteroaryl structures comprising triarylsilyl(meth) acrylate of unit A of the seawater erodible polymer of randomly recurring units of polymer of formula -[A]-[B]— in which A represents from above 9 to about 20 mole percent of the polymer and the "aryl" group is selected from phenyl, o-tolyl, in-tolyl, p-tolyl, 4-trifluoromethylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,6-trimethylphenyl, o-fluorophenyl, o-chlorophenyl, o-bromophenyl, o-ethylphenyl, m-fluorophenyl, m-chlorophenyl, m-bromophenyl, p-fluorophenyl, p-chlorophenyl, p-bromophenyl, p-ethylphenyl, p-propylphenyl, p-n-butylphenyl, p-t-butylphenyl, 2,3-difluorophenyl, 2,6-difluorophenyl, 2,6-dichlorophenyl, 2,3-dichlorophenyl, 2-methyl-4-fluorophenyl, 2-fluoro-5-methylphenyl, 3-fluoro-4-methylphenyl, 3-methyl-4-fluorophenyl, 2-methyl-3-fluorophenyl, 3,4-difluorophenyl, 2,5-difluorophenyl, 2,4-difluorophenyl, 3,4-dichlorophenyl, 2, 4-dichlorophenyl, 2-methyl-4-chlorophenyl, 2,5-dichlorophenyl, 3,5-difluorophenyl, 3, 5-dibromophenyl, 3,5-dichlorophenyl, 2,3,4-trifluorophenyl, 2,4,6-trifluorophenyl, 2,3,5-trifluorophenyl, 3,4,5-trifluorophenyl, 2,6-dichloro-4-trifluoromethylphenyl, 2,4,6-tri-t-butylphenyl, 2,4,5-trifluorophenyl, 2,4,5-trimethylphenyl, 2,3,5,6-tetrafluorophenyl, 2,3,4,5-tetrafluorophenyl, 2,3,4,6-tetrafluorophenyl, 2,3,5,6-tetramethylphenyl, pentafluorophenyl, 2,3,5,6-tetrafluoro-4-bromophenyl, o-trifluoromethyl, m-trifluoromethyl, p-trifluoromethyl, 2-chloro-5-trifluoromethylphenyl, 2-trifluoromethyl-3-chlorophenyl, 2,4-bis(trifluoromethyl)phenyl, 3,5-bis(trifluoromethyl)phenyl, 2-biphenyl, 3-biphenyl, 4-biphenyl, 2-methyl-3-biphenyl, 2-fluoro-4-biphenyl, 1-naphthyl, 2-naphthyl, 2-methyl-1-naphthyl, 4-methyl-1-naphthyl, 5-acenaphthenyl, 2-fluorenyl, 1-anthracenyl, 2-anthracenyl, 9-anthracenyl, 9-phenanthrenyl, 1-pyrenyl, 2-methoxyphenyl, 3-methoxyphenyl, 4-methoxyphenyl, 4-ethoxyphenyl, 2-methyl-4-methoxyphenyl, 2-methoxy-5-fluorophenyl, 3,4-dimethoxyphenyl, 2,4-dimethoxyphenyl, 2,5-dimethoxyphenyl, 3,5-dimethoxyphenyl, 2,4-difluoro-6-methoxyphenyl, 2,4-dimethoxy-6-fluorophenyl, 4-phenoxyphenyl, 6-methoxy-2-naphthalenyl, 4-dimethylaminophenyl, 2-trifluoromethyl-4-dimethylaminophenyl, 2-trifluoromethyl-4-dimethylaminophenyl, 3-[N,N-bis(trimethylsilyl)amino]phenyl, 4-[N,N-bis(trimethylsilyl)amino]phenyl-2-thienyl, 3-thienyl, 1-methyl-5-imidazolyl, 1-ethyl-2-methyl-5-imidazolyl, 2-benzoxazolyl, 2-methyl-5-benzoxazolyl, 2-methyl-5-benzothiazolyl, 2-pyridinyl, 4-methyl-2-pyridinyl, 4-pyridinyl, 6-methyl-2-pyridinyl, 5-trifluoromethyl-2-pyridinyl, 6-(2,2'-bipyridinyl), 4'-(2,2':6',2''-terpyridinyl), 2-fluoro-5-trifluoromethyl-3-pyridinyl, 2,3,5,6-tetrafluoropyridinyl, 6-methoxy-2-pyridinyl, 6-phenyl-3-pyridazinyl, 6-methoxy-3-pyridazinyl, 2-pyrimidinyl, 5-pyrimidinyl, 4-trifluoromethyl-2-pyrimidinyl, 2,4,6-trifluoro-5-pyrimidinyl, 2,4-dimethoxy-6-pyrimidinyl, pyrazinyl, 2-quinolinyl, 4-quinolinyl, 6-quinolinyl, 8-quinolinyl, 7-trifluoromethyl-4-quinolinyl, 8-trifluoromethyl-4-quinolinyl, 2,8-bis(trifluoromethyl)-4-quinolinyl, 3-quinolinyl, 4-quinaldinalyl, 7-quinaldinalyl, 2-lepidinyl, 4-isoquinolyl, 5-(1,10-phenanthrolinyl). The preferred aryl group is phenyl.

B represents the residue of two or more ethylenically unsaturated monomers copolymerizable with the triarylsilyl (meth)acrylate. The properties of the polymer can be modified by adding hydrophilic or hydrophobic functionality by way of the monomer or combination of monomers comprising B. Useful monomers include the esters of acrylic acid such as methyl acrylate, ethyl acrylate, propyl acrylate, n-butyl acrylate, t-butyl acrylate, sec-butyl acrylate, 2-ethylhexyl acrylate, cyclohexyl acrylate, phenyl acrylate, n-octyl acrylate, 2-hydroxyethyl acrylate, hydroxy-n-propyl acrylate, hydroxy-i-propyl acrylate, glycidyl acrylate, 2-methoxyethyl acrylate, 2-methoxypropyl acrylate, methoxytriethyleneglycol acrylate, 2-ethoxyethyl acrylate, ethoxydiethyleneglycol acrylate and the esters of methacrylic acid such as methyl methacrylate, ethyl methacrylate, propyl methacrylate, n-butyl methacrylate, t-butyl methacrylate, sec-butyl methacrylate, 2-ethylhexyl methacrylate, cyclohexyl methacrylate, 2-hydroxyethyl methacrylate, glycidyl methacrylate, 2-methoxyethyl methacrylate, 2-methoxypropyl methacrylate, methoxytriethyleneglycol methacrylate, and 2-ethoxyethyl methacrylate, hydroxy-n-propyl(meth)acrylate, hydroxy-i-propyl methacrylate, phenoxyethyl methacrylate, butoxy ethyl methacrylate, isobornyl (meth)acrylate. Other useful ethylenically unsaturated monomers include neopentyl glycolmethylether propoxylate acrylate, poly(propylene glycol) methylether acrylate, ethoxydiethyleneglycol methacrylate, acrylic acid, methacrylic acid, 2-butoxyethyl acrylate, crotonic acid, di(ethylene glycol) 2-ethylhexyl ether acrylate, di(ethylene glycol) methyl ether methacrylate, 3,3-dimethyl acrylic acid, 2-(dimethylamino) ethyl acrylate, 2-(dimethylamino) ethyl methacrylate, ethylene glycol phenyl ether acrylate, ethylene glycol phenyl ether methacrylate, 2(5H)-furanone, hydroxybutyl methacrylate, methyl-2(5H)-furanone, methyl trans-3-methoxyacrylate, 2-(t-butylamino) ethyl methacrylate, tetrahydrofurfuryl acrylate, 3-tris-(trimethylsiloxy)silyl propyl methacrylate, tiglic acid, and trans-2-hexenoic acid.

Other examples of polymerizable monomers include vinyl esters such as vinyl acetate, vinyl propionate, vinyl butyrate, vinyl benzoate, maleic esters such as dimethyl maleate, diethyl maleate, di-n-propyl maleate, diisopropyl maleate, di-2-methoxyethyl maleate, fumaric esters such as dimethyl fumarate, diethyl fumarate, di-n-propyl fumarate, diisopropyl fumarate, styrene, vinyltoluene, alpha-methylstyrene, N,N-dimethyl acrylamide, N-t-butyl acrylamide, N-vinyl pyrrolidone, and acrylonitrile.

Additional monomers useful in the production of polymers of the invention include: trialkylsilyl(meth)acrylates such as trimethylsilyl(meth)acrylate, diphenylmethylsilyl (meth)acrylate, phenyidimethylsilyl(meth)acrylate, triisopropylsilyl (meth)acrylate, and tributylsilyl(meth)acrylate.

The polymers of the present invention are prepared by polymerizing triarylsilyl(meth)acrylate with one or more ethylenically unsaturated monomers which are copolymerizable therewith. When at least two monomers are copolymerized with triarylsilyl(meth)acrylate to form a polymer, it is generally called a terpolymer or higher polymer. Specific monomers have been discovered to be useful in synthesizing terpolymers or higher polymers of the present invention to provide polymers with improved properties such as film flexibility and crack resistance, while retaining acceptable water erodibility. N-octyl acrylate is an example of a monomer that improves film properties when polymerized into a terpolymer composition. Table 5 contains data showing the beneficial effect on the resulting polymer achieved with such termonomers.

The triarylsilyl(meth)acrylate component represents from above 9 to about 20 mole percent of the polymer. This range provides a polymer having an erosion rate in seawater of from 2 to about 15 microns/month. Preferably, the triarylsilyl(meth)acrylate component is present in an amount to provide a polymer having an erosion rate from about 3 to about 9 microns/month. The amounts of triarylsilyl(meth) acrylate monomer can be selected and adjusted within the range of above 9 to about 20 mole percent of the polymer to provide a polymer having an erosion rate of from about 2 to about 15 microns/month, preferably from about 3 to about 9 microns/month and optimally from about 3 to about 7 microns/month. Also preferred is a polymer that provides a reasonably uniform erosion rate for the marine antifouling paint.

While most of the prior art evaluates the erosion rate of marine antifouling paints, the present invention measures the erosion rate of the polymer binder. It has been found that measuring the erosion rate of candidate films for 60±5 days provides a basis for identifying and excluding those polymers that erode too quickly or too slowly to be the basis of a satisfactory paint. From the data in FIG. 1, it is seen that films containing 5, 6, and 9 mole percent triphenylsilyl methacrylate erode too slowly to pass a 65-day test. Specifically, it is observed that, while the erosion rates of the polymers containing 6 and 9 mole percent exceed 2 microns/month during the early part of the test, they gradually decrease so that after about 40 days the erosion rates are below 2 microns/month. It is also observed that films containing 25 mole percent triphenylsilylmethacrylate and above erode too quickly. While the erosion rate of the 25 mole percent polymer begins inside the desired 2 to 15 microns/month range, by about 25 days the erosion rate has increased to a level well above 15 microns/month. The films containing 16 and 20 mole percent of triphenylsilylmethacrylate display erosion rates in the range of about 3 to about 9 microns per month during a 65-day erosion test and these are comparable to the erosion performance of BIOMET 304, a commercially available (from ATOFINA Chemicals, Inc.) triorganotin-containing polymer. Thus, polymer compositions having a triarylsilyl(meth)acrylate content in the range of above 9 to about 20 mole percent have erosion rates comparable to those of the organotin-containing polymers that are the standard of the industry.

TABLE 1

| Mole % | 65 DAY TEST |
|---|---|
| 5 | FAIL |
| 6 | FAIL |
| 9 | FAIL |
| 16 | PASS |
| 20 | PASS |
| 25 | FAIL |

The data in Tables 1, 3 and 4 establish that a mole percent range for monomer A of from above 9 mole percent to about 20 mole percent produces a polymer that passes the erosion rate test and therefore has an erosion rate suitable for use in a marine antifouling paint. Such polymers have an erosion rate in seawater of from about 2 to about 15 microns/month as determined by testing in accordance with the rotor test described hereinafter and when tested a period of 60±5 days. Thus, it is seen that it is only within a narrow band of mole percentages of from above 9 mole percent to about 20 mole percent that triarylsilyl(meth)acrylate polymers have erosion rates comparable to those of the triorganotin-containing polymers and are therefore suitable for use in marine antifouling paints. Therefore, the polymers of the present invention are suitable for formulating a marine antifouling paint having a multi-year useful life on an ocean-going vessel similar to the useful life achievable with triorganotin-containing polymers of 3 to 5 years.

In general, the erosion rate is considered to be a function of the amount of hydrolysable monomer in the polymer. Indeed, U.S. Pat. No. 4,593,055, which discloses and claims seawater erodible organosilylacrylate copolymers, teaches at Column 5, lines 43 et seq. that the superior control of the erosion rate relies on chemically tailoring the polymer so that it is selectively weakened at certain points pendant to the polymer chain at the paint/water interface. These weak links are slowly attacked by seawater allowing the polymer to gradually become seawater soluble or seawater swellable. This weakens the hydrolysed surface polymer film to such an extent that moving seawater is able to wash off this layer and thus expose a fresh surface.

A portion of the monomeric units provides functional groups which provide a site of weakness, that is, sites which tend to hydrolyze in the presence of seawater. The ratio of functionalized monomers to non-functionalized monomers is selected to provide control of the erosion rate.

Figure 1:
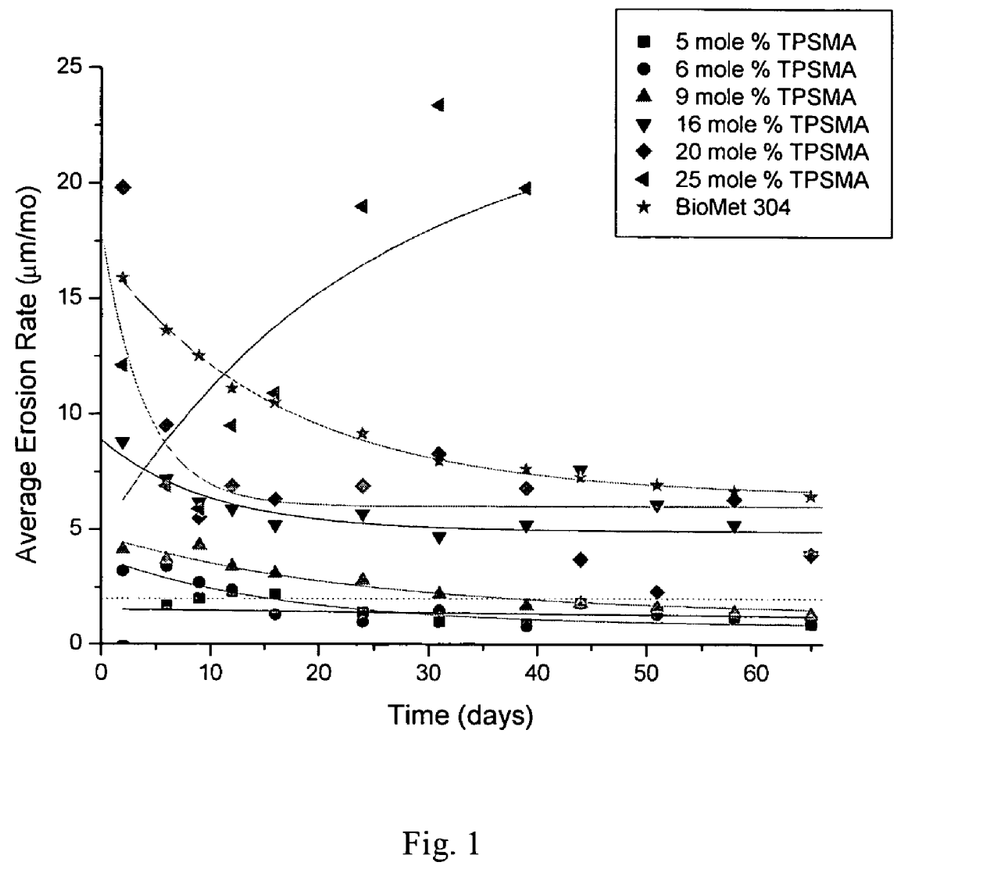
FIG. 1 illustrates the relationship between mole percent triphenylsilyl(meth)acrylate residue in a polymer and the erosion rate in seawater of the polymer and compares those erosion rates with that of a triorganotin-based polymer. Each phenyl group can be substituted or un-substituted or a heterocyclic aromatic group and each can be the same or different.

The proposition, illustrated in FIG. 1, that at levels below 9 mole percent and above about 20 mole percent of triarylsilyl(meth)acrylate the erosion rate is not satisfactory, is wholly surprising and unexpected, particularly in view of the prior art teaching that organosilylacrylate levels in the range of 25 to 50 mole percent should be used in order to obtain useful polymers.

The polymers of the present invention will contain from above 9 to about 20 mole percent of triarylsilyl(meth)acrylate component and correspondingly from below 91 to about 80 mole percent of one or more ethylenically unsaturated monomers that are copolymerizable with triarylsilyl (meth)acrylate.

While the data in the present discussion has focused on erosion rate, the amount of triarylsilyl(meth)acrylate monomer present in conjunction with one or more ethylenically unsaturated monomers can be optimized to address other properties such as film lifetime, erosion rate uniformity, ease of processing, ease of formulation, biocide compatibility, shelf-life, adhesion, crack-resistance, flexibility, and economics.

The random triarylsilyl(meth)acrylate polymer can be obtained by polymerizing the mixture of monomers in the presence of a free-radical olefinic polymerization initiator or catalyst using any of various methods such as solution polymerization, bulk polymerization, emulsion polymerization, and suspension polymerization using methods well-known and widely used in the art. In preparing a coating composition from the polymer, it is advantageous to dilute the polymer with an organic solvent to obtain a polymer solution having a convenient viscosity. For this, it is also desirable to employ the solution polymerization method or bulk polymerization method.

Examples of olefinic polymerization initiators include azo compounds such as 2,2'-azobis (isobutyronitrile) and triphenylmethylazobenzene. The azobisnitriles are efficient sources of free radicals for vinyl polymerization and can be used in bulk, solution, emulsion, and suspension polymerizations. In addition to 2,2'-azobis (isobutyronitrile), other members of the class include 2,2'-azobis(2-methylbutanenitrile), 2,2'-azobis(2,4-dimethylpentanenitrile), 1,1'-azobis (cyanocyclohexane) and 2,2'-azobis(4-methoxy-2,4-dimethylpentanenitrile). One can also use peroxides such as benzoyl peroxide, di-t-butyl peroxide, t-butyl peroxybenzoate, and t-butyl peroxyisopropylcarbonate.

Examples of useful organic solvents include aromatic hydrocarbons such as xylene and toluene, aliphatic hydrocarbons such as hexane and heptane, esters such as ethyl acetate and butyl acetate, alcohols such as isopropyl alcohol and butyl alcohol, ethers such as dioxane and tetrahydrofuran, and ketones such as methyl ethyl ketone and methyl isobutyl ketone. The solvents are used either alone or in combination.

The desirable molecular weight of the triarylsilyl(meth) acrylate-containing polymer thus obtained is in the range of from 1,000 to 200,000 g/mol, preferably from 10,000 to 150,000 g/mol in terms of weight-average molecular weight. Too low or too high molecular weight polymers create difficulties in forming normal coating films. Too high molecular weights result in long, intertwined polymer chains that do not perform properly and result in viscous solutions that need to be thinned with solvent so that a single coating operation results in a thin film coating. Too low molecular weight polymers require multiple coating operations and provide films that may lack integrity and do not perform properly. It is advantageous that the viscosity of the solution of the polymer is 200 to 6,000 centipoise at 25° C. To achieve this, it is desirable to regulate the solid content of the polymer solution to a value in the range of from 5 to 90% by weight, desirably from 15 to 85% by weight.

The toxicant used in the coating composition of the present invention may be any of a wide range of conventionally known toxicants. The known toxicants are roughly divided into inorganic compounds, metal-containing organic compounds, and metal-free organic compounds.

Examples of inorganic toxicant compounds include copper compounds such as cuprous oxide, copper powder, copper thiocyanate, copper carbonate, copper chloride, and copper sulfate, and zinc and nickel compounds such as zinc sulfate, zinc oxide, nickel sulfate, and copper-nickel alloys.

Examples of metal-containing organic toxicant compounds include organocopper compounds, organonickel compounds, and organozinc compounds. Examples of organocopper compounds include oxine copper, copper nonylphenolsulfonate, copper bis (ethylenediamine) bis (dodecylbenzenesulfonate), copper acetate, copper naphthenate, and copper bis (pentachlorophenolate). Examples of organonickel compounds include nickel acetate and nickel dimethyldithiocarbamate. Examples of organozinc compounds include zinc acetate, zinc carbamate, zinc dimethyldithiocarbamate, zinc pyrithione, and zinc ethylenebis (dithiocarbamate).

Examples of metal-free organic toxicant compounds include N-trihalomethylthiophthalimides, dithiocarbamic acids, N-arylmaleimides, 3-(substituted amino)-1,3-thiazolidine-2,4-diones, dithiocyano compounds, triazine compounds, and others.

Examples of N-trihalomethylthiophthalimide toxicants include N-trichloromethylthiophthalimide and N-fluorodichloromethylthiophthalimide. Examples of dithiocarbamic toxicants include bis (dimethylthiocarbamoyl) disulfide, ammonium N-methyidithiocarbamate, and ammonium ethylenebis (dithiocarbamate).

Examples of arylmaleimide toxicants include N-(2,4,6-trichlorophenyl)maleimide, N-4-tolylmaleimide, N-3-chlorophenylmaleimide, N-(4-n-butylphenyl)maleimide, and N-anilinophenyl)maleimide.

Examples of 3-(substituted amino)-1,3-thiazolidine-2,4-dione toxicants include 3 benzylideneamino-1,3 thiazolidine-2,4-dione, 3-4(methylbenzylideneamino), 1,3-thiazolidine-2,4-dione, 3-(2-hydroxybenzylideneamino-1,3-thiazolidine-2,4-thiazolidine-2,4-dione, 3-(4-dichlorobenzylideneamino)-1,3-thiazolidine-2,4-dione and 3-(2,4-dichlorobenzylideneamino-1,3-thiazolidine-2,4-dione.

Examples of dithiocyano toxicant compounds include dithiocyanomethane, dithiocyanoethane, and 2,5-dithiocyanothiophene. Examples of the triazine compounds include 2-methylthio-4-t-butylamino-6-cyclo-propylamino-s-triazine.

Other examples of metal-free organic toxicant compounds include 2,4,5,6-tetrachloroisophthalonitrile, N,N-dimethyidichlorophenylurea, 4,5-dichloro-2-n-octyl-4-isothiazoline-3-one, N,N-dimethyl-N'-phenyl-(N-fluorodichloromethylthio)sulfamide, tetramethylthiuram disulfide, 3-iodo-2-propylbutyl carbamate, 2-(methoxycarbonylamino) benzimidazole, 2,3,5,6-tetrachloro-4-(methylsulfonyl) pyridine and diiodomethyl-p-tolyl sulfone.

One or more toxicants, which may be selected from the foregoing toxicants, can be employed in the antifoulant coating composition. The toxicant is used in an amount from 0.1 to 80% by weight, preferably from 1 to 60% by weight of the coating composition. Too low toxicant levels do not produce an antifouling effect, while too large a toxicant level can result in the formation of a coating film which is liable to develop defects such as cracking and peeling, thereby, becoming less effective.

Additive ingredients may optionally be incorporated into the coating composition of the present invention. Examples of such additive ingredients are colorants such as pigments (e.g., red iron oxide, zinc oxide, titanium dioxide, talc), and dyes, stabilizers, dehumidifiers, and additives ordinarily employed in coating compositions such as antisagging agents, antiflooding agents, antisettling agents, and antifoaming agents.

Triarylsilyl(meth)acrylate polymers and coating compositions made from these polymers may increase in viscosity during storage. To prevent an unsatisfactory viscosity increase, materials known as "stabilizers" may be added during or after polymerization or may be incorporated into the coating composition. Stabilizing materials include inorganic dehydrating agents, such as molecular sieves or anhydrous calcium sulfate; organic dehydrating agents, such as orthoesters; bases, such as amino compounds; water reactives, such as alkoxy silanes; chelating agents, such as tris nonylphenylphosphite; and hindered phenol antioxidants, such as butylated hydroxy toluene (BHT). In normal use, the stabilizer level is 0.1 to 10 weight percent based on the coating composition.

Rosin and rosin derivatives may be added to the coating composition as part of the binder system. Rosin and rosin derivatives are preferably present in the range of 5 to 60 weight percent of the polymer, preferably 10 to 30 weight percent for the purpose of assisting in controlling water penetration into the coating film.

For applying the marine antifouling coating compositions made from the triarylsilyl(meth) acrylate polymers of the present invention onto the surface of a marine vessel, the coating composition is applied to the surface in a suitable manner (such as by brushing or spraying) and the solvent is removed by evaporation at ambient temperature or with heating. By this method, a dry coating film of suitable thickness can be easily formed on the surface of the vessel.

In addition to marine antifouling applications, the antifouling coating composition of the invention may also be used in fresh water and brackish water applications.

General Polymerization Procedure

Xylene was injected into a microreactor equipped with a condenser, an inert gas/vacuum line connector, two variable speed syringe pumps, septum inlet, temperature control of ±2° C. and mechanical agitation. The xylene was heated to 86° C. and held at that temperature for 10 minutes. The syringe pumps were then turned on and a mixture of the monomers, initiator (2,2'-azobis(isobutyronitrile)), and xylene was added over a period of 1 hour. The reaction mixture was held at −86° C. for an additional 3 hours, whereupon the temperature was raised to 110° C. and held at this level for 10 minutes. The heating was then discontinued and the reactor was allowed to cool to room temperature. The monomers in this experiment were triphenylsilylmethacrylate (TPSMA) and methylmethacrylate (MMA). The compositions are summarized in Table 2 below.

TABLE 2

| Mole % TPSMA | Mole % MMA | Monomer/Initiator Ratio |
| --- | --- | --- |
| 5.1 | 94.9 | 215 |
| 5.1 | 94.9 | 215 |
| 6.1 | 93.9 | 215 |
| 6.1 | 93.9 | 215 |
| 9.1 | 90.9 | 215 |
| 9.1 | 90.9 | 215 |
| 16.2 | 83.8 | 216 |
| 16.2 | 83.8 | 215 |
| 16.2 | 83.8 | 215 |
| 20.2 | 79.8 | 216 |
| 20.2 | 79.8 | 215 |
| 25.3 | 74.7 | 216 |
| 25.2 | 74.8 | 216 |

Rotor Test

Figure 2:
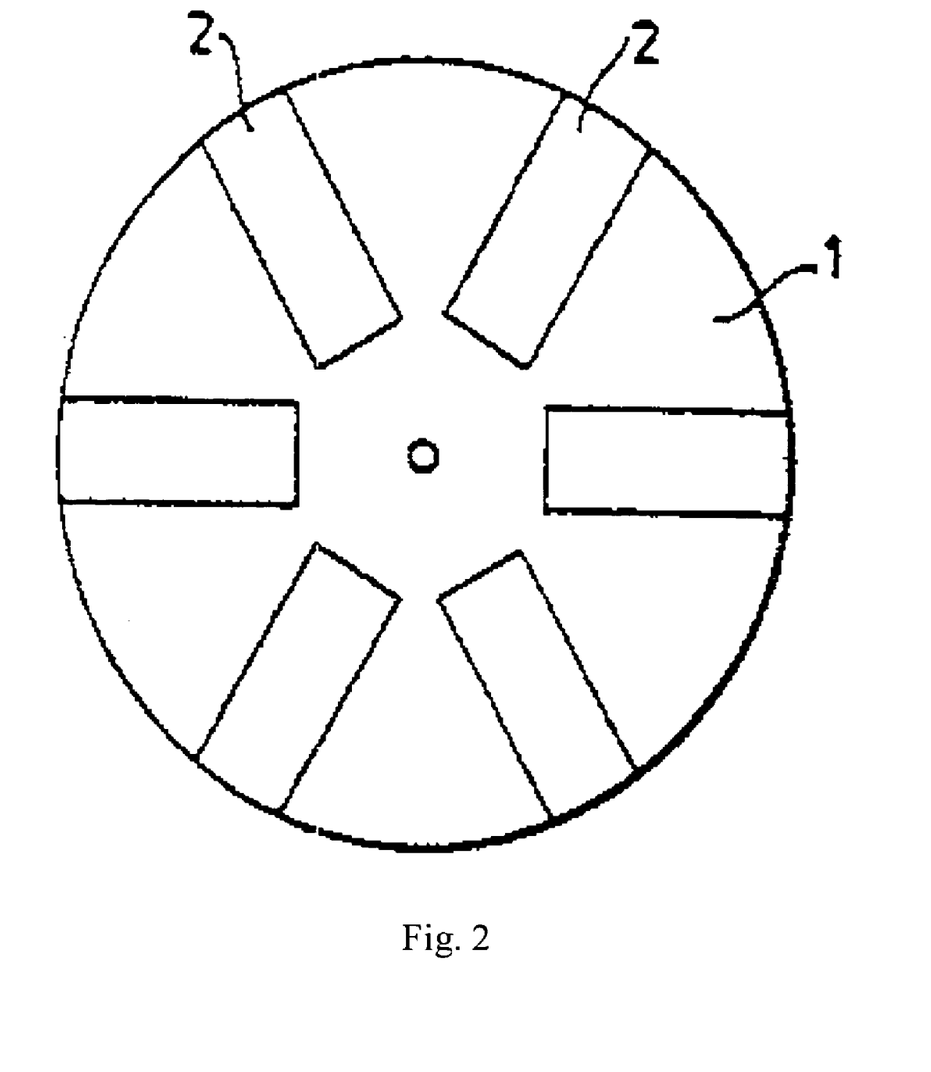
FIGS. 2 and 3 illustrate the rotor test apparatus used to determine erosion rate.
Figure 3:
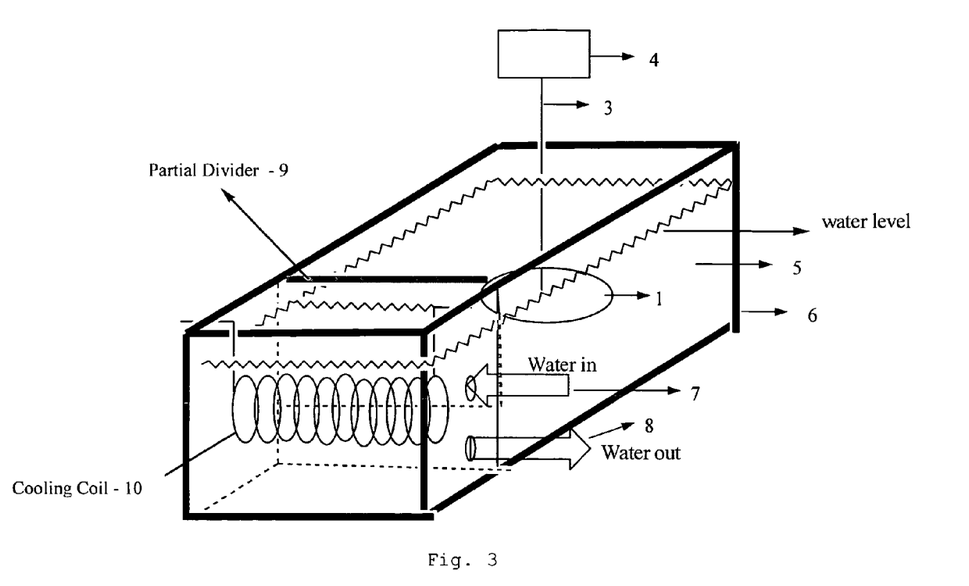

The performance of the polymers in relatively moving seawater was tested in the apparatus illustrated schematically in FIGS. 2 and 3 of the drawings. Referring to these Figures, a poly (methylmethacrylate) disc 1 having a diameter of 8 inches was coated with radial stripes 2 with the polymer undergoing testing being applied from an applicator adapted to deposit a film. The disc 1 was set aside to dry and the thickness of the stripes 2 was measured by contact profilometry using a Tencor Alpha Step 500 Profiler.

The disc 1 was mounted on a shaft 3 driven by an electric motor 4 and immersed in flowing seawater 5 contained in a vessel 6 having an inlet 7 and an outlet 8. A pump (not shown) is used to circulate seawater from outlet 8 through a filter (not shown) and back to vessel 6 through inlet 7. Cooling fluid is circulated through cooling coils 10 to maintain the seawater temperature. Partial divider, 9, extends from above the water surface to just below the depth of the cooling coils. The peripheral speed of the disc 1 at the measured circumference point (8.0 cm radius) was 17 knots and the seawater temperature was maintained at 20±3° C. Failure to control the test temperature has consequences. Higher temperatures result in faster erosion, while lower temperatures cause slower erosion.

During this test, the stripes were eroded away from the disc. The film thickness was measured periodically during the rotor test for each stripe at the 8.0 cm radius point and the rate of removal of polymer by erosion was determined. The Rotor Test is conducted for 60±5 days in seawater and the erosion rate is calculated in microns per month (μ/mo) from film thickness measurements as a function of time. The erosion rate in seawater so calculated is defined herein as the "Erosion Rate" and referred to as a "65 day Erosion Rate test". FIG. 1 is a plot of Erosion Rate versus time for polymer samples having various mole percents of triarylsilyl (meth)acrylate. FIG. 1 shows that the Erosion Rate of the polymer was most closely related to that of a reference triorganotin-containing polymer when the triarylsilyl(meth)acrylate content was in the range of above 9 to about 20 mole percent.

Rotor tests were conducted for two series of terpolymers comprising triphenylsilyl methacrylate, methyl methacrylate, and a third monomer as specified in the table. The Erosion Rate results are shown in Tables 3 and 4. Table 4 demonstrates conclusively that the compositions having less than 9 mole percent of triarylsilylmethacrylate do not have satisfactory Erosion Rates. Conversely, Table 3 demonstrates conclusively that terpolymers having about 10 to about 15 mole percent triarylsilylmethacrylate have satisfactory Erosion Rates.

TABLE 3

| Example | [3rd Monomer] | MMA-TPSMA-[3rd] Composition | Mw (g/mol) | PDI | 8-week ER (μ/mo) |
|---|---|---|---|---|---|
| 1 | DEF | 80-15-5 | 38,000 | 1.9 | 4.6 |
| 2 | PEMA | 80-15-5 | 61,000 | 2.3 | 3.5 |
| 3 | HPA | 72-15-13 | 123,000 | 3.2 | 3.4 |
| 4 | DEF | 87-10-3 | 63,000 | 2.2 | 3.3 |
| 5 | HPA | 83-10-7 | 84,000 | 2.3 | 3.0 |
| 6 | HPA | 77-10-13 | 132,000 | 3.0 | 2.9 |
| 7 | HPA | 78-15-7 | 82,000 | 2.5 | 2.8 |
| 8 | DEGEHA | 75-15-10 | 135,000 | 4.0 | 2.8 |
| 9 | DMAEMA | 87-10-3 | 43,000 | 1.9 | 2.5 |
| 10 | BEA | 85-10-5 | 46,000 | 1.9 | 2.4 |
| 11 | PEMA | 85-10-5 | 115,000 | 2.6 | 2.4 |
| 12 | HBMA | 75-15-10 | 62,000 | 2.3 | 2.4 |
| 13 | EGMEA | 82-15-3 | 73,000 | 2.3 | 2.3 |
| 14 | HBMA | 80-15-5 | 69,000 | 2.3 | 2.3 |
| 15 | DMAA | 80-15-5 | 59,000 | 2.3 | 2.2 |
| 16 | HPA | 80-10-10 | 120,000 | 3.0 | 2.2 |
| 17 | PEMA | 82-15-3 | 111,000 | 2.5 | 2.1 |
| 18 | HPA | 77-10-13 | 92,000 | 2.6 | 2.1 |
| 19 | DEGEHA | 80-15-5 | 61,000 | 2.5 | 2.0 |
| 20 | THFA | 77-10-13 | 112,000 | 3.4 | 2.0 |

DEF = diethyl fumarate;
PEMA = ethylene glycol phenyl ether methacrylate;
HPA = hydroxypropyl acrylate;
DEGEHA = di(ethylene glycol) ethylhexyl acrylate;
DMAEMA = (dimethylamino)ethyl methacrylate;
BEA = butoxyethyl acrylate;
HBMA = hydroxybutyl methacrylate;
EGMEA = ethylene glycol methyl ether acrylate;
DMAA = 3,3-dimethylacrylic acid;
THFA = tetrahydrofurfuryl acrylate

TABLE 4

| Example | [3rd Monomer] | MMA-TPSMA-[3rd] Composition | Mw (g/mol) | PDI | 8-week ER (μ/mo) |
|---|---|---|---|---|---|
| A | DEGEEMA | 92-5-3 | 79,000 | 2.7 | 0.7 |
| B | DEGEEMA | 90-5-5 | 65,000 | 2.4 | 1.1 |
| C | DEGEEMA | 85-5-10 | 128,000 | 4.0 | 1.5 |
| D | EGMEA | 85-5-10 | 56,000 | 2.2 | 1.6 |
| E | EGMEA | 90-5-5 | 63,000 | 2.2 | 1.0 |
| F | EGMEA | 92-5-3 | 63,000 | 2.5 | 0.8 |
| G | EGMEA | 90-5-5 | 99,000 | 2.8 | 0.5 |
| H | EGMEA | 92-5-3 | 113,000 | 2.8 | 1.4 |
| I | THFA | 82-5-13 | 115,000 | 3.8 | 1.5 |
| J | THFA | 85-5-10 | 71,000 | 2.5 | 1.7 |
| K | THFA | 88-5-7 | 74,000 | 2.3 | 1.2 |
| L | BEA | 85-5-10 | 48,000 | 1.9 | 1.6 |
| M | BEA | 92-5-3 | 58,000 | 2.1 | 1.2 |
| N | DEF | 92-5-3 | 57,000 | 2.1 | 1.8 |
| O | DEF | 90-5-5 | 43,000 | 2.0 | 1.1 |
| P | DEF | 87-5-8 | 56,000 | 2.1 | 1.0 |
| Q | MAA | 94-5-1 | 51,000 | 2.1 | 0.8 |
| R | HPA | 82-5-13 | 67,000 | 2.2 | 1.5 |
| S | HPA | 85-5-10 | 66,000 | 2.3 | 1.9 |
| T | HPA | 88-5-7 | 61,000 | 2.1 | 1.2 |
| U | PEMA | 85-5-10 | 89,903 | 2.6 | 0.6 |
| V | PEMA | 90-5-5 | 65,838 | 2.3 | 0.9 |
| W | PEMA | 92-5-3 | 64,474 | 2.3 | 1.3 |
| X | HPA | 88-5-7 | 75,000 | 2.2 | 1.1 |

DEGEEMA = di(ethylene glycol) ethyl ether methacrylate;
EGMEA = ethylene glycol methyl ether acrylate;
THFA = tetrahydrofurfuryl acrylate;
BEA = butoxyethyl acrylate;
DEF = diethyl fumarate;
MAA = methacrylic acid;
HPA = hydroxypropyl acrylate;
PEMA = phenoxyethyl methacrylate;
HPMA = hydroxypropyl methacrylate;

Polymers were prepared using the general polymerization procedure described above. The monomers and their parts by mol. percent used to make each polymer are given in Tables 3, 4, and 5. Each polymer in Table 5 was tested for flexibility using a method based on ASTM D-522 (cylindrical mandrel test). The flexibility of the polymer was rated on the scale of 1 to 5 with 1 being the least flexible. The erosion performance for each polymer was also tested using the Rotor Test described above; the results are given in Table 5. As can be seen from Table 5, the terpolymers exhibit superior film flexibility while maintaining acceptable erosion rate performance.

TABLE 5

| Example | MMA-TPSMA-nOA Composition | Mw (g/mol) | PDI | Flexibility | 8-week ER (µ/mo) |
|---------|---------------------------|------------|------|-------------|------------------|
| A | 83-17-0 | 57,000 | 1.97 | 1 | |
| B | 73-17-10 | 40,000 | 2.02 | 2 | 3.4 |
| C | 62-17-21 | 69,000 | 1.93 | 5 | 3.6 |
| D | 58-17-25 | 43,000 | 2.11 | 3 | 3.5 | nOA = n-octyl acrylate

We claim:

1. A terpolymer having an Erosion Rate in seawater that is suitable for use as a binder in a marine antifouling paint and having improved flexibility comprising
    a) a polymer of the formula -[A]-[B]- where A is present from above 9 to less than 20 mole percent based on the total molar amount of monomers used to make the polymer(s) comprising the marine antifouling paint, and comprises one or more triarylsilyl(meth)acrylol groups (—XSiR$_3$) wherein each R may be the same or different and is a substituted or unsubstituted aryl or heteroaryl group, X is the residue of an acryloxy or methacryloxy group; and B represents the residue of methyl methacrylate and one or more other different ethylenically unsaturated monomers copolymerizable with A, and wherein the terpolymer is characterized by an Erosion Rate in sea water of from 2 to 15 microns per month; and
    b) one or more stabilizing agent(s) selected from a dehydrating agent, a zeolite, an acid neutralizer, an amino containing compound, an antioxidant, a chelator, and/or an alkoxy silane.

2. The seawater erodible terpolymer of claim 1 in which at least one R is an unsubstituted aryl, an aryl group substituted with one or more chlorine, fluorine, bromine, iodine, alkyl, perfluoroalkyl, napthyl, fluorenyl, anthracenyl, phenanthrenyl, pyrenyl, alkylether, substituted alkylether, arylether, substituted arylether, amino substituted group, or mixtures thereof.

3. The seawater erodible terpolymer of claim 1 wherein A is triphenylsilylacrylate or triphenylsilylmethacrylate, and the polymer is characterized by an Erosion Rate in seawater of from 2 to 15 microns per month.

4. The seawater erodible terpolymer of claim 1 in which at least one R is a sulfur-, nitrogen-, or oxygen-containing heteroaryl group.

5. The seawater erodible terpolymer of claim 1 in which B represents the residue of methyl methacrylate and one or more other ethylenically unsaturated monomers selected from the group consisting of unsaturated organic acids, esters of acrylic acid, esters of methacrylic acid, vinyl compounds, maleic esters, and fumaric esters.

6. The seawater erodible terpolymer of claim 5 in which B is selected from methyl acrylate, ethyl acrylate, propyl acrylate, n-butyl acrylate, t-butyl acrylate, sec-butyl acrylate, 2-ethylhexyl acrylate, cyclohexyl acrylate, phenyl acrylate, n-octyl acrylate, 2-hydroxyethyl acrylate, hydroxy-n-propyl acrylate, hydroxy-i-propyl acrylate, glycidyl acrylate, 2-methoxyethyl acrylate, 2-methoxypropyl acrylate, methoxytriethyleneglycol acrylate, 2-ethoxyethyl acrylate, ethoxydiethyleneglycol acrylate, methyl methacrylate, ethyl methacrylate, propyl methacrylate, n-butyl methacrylate, t-butyl methacrylate, sec-butyl methacrylate, 2-ethylhexyl methacrylate, cyclohexyl methacrylate, 2-hydroxyethyl methacrylate, glycidyl methacrylate, 2-methoxyethyl methacrylate, 2-methoxypropyl methacrylate, methoxytriethyleneglycol methacrylate, and 2-ethoxyethyl methacrylate, hydroxy-n-propyl(meth)acrylate, hydroxy-i-propyl methacrylate, phenoxyethyl methacrylate, butoxy ethyl methacrylate, isobornyl (meth)acrylate, neopentyl glycolmethylether propoxylate acrylate, poly(propylene glycol) methylether acrylate, ethoxydiethyleneglycol methacrylate, acrylic acid, methacrylic acid, 2-butoxyethyl acrylate, crotonic acid, di(ethylene glycol) 2-ethylhexyl ether acrylate, di(ethylene glycol) methyl ether methacrylate, 3,3-dimethyl acrylic acid, 2-(dimethylamino) ethyl acrylate, 2-(dimethylamino) ethyl methacrylate, ethylene glycol phenyl ether acrylate, ethylene glycol phenyl ether methacrylate, 2(5H)-furanone, hydroxybutyl methacrylate, methyl-2(5H)-furanone, methyl trans-3-methoxyacrylate, 2-(t-butylamino) ethyl methacrylate, tetrahydrofurfuryl acrylate, 3-tris-(trimethylsiloxy)silyl propyl methacrylate, tiglic acid, trans-2-hexenoic acid, vinyl acetate, vinyl propionate, vinyl butyrate, vinyl benzoate, dimethyl maleate, diethyl maleate, di-n-propyl maleate, diisopropyl maleate, di-2-methoxyethyl maleate, dimethyl fumarate, diethyl fumarate, di-n-propyl fumarate, diisopropyl fumarate, styrene, vinyltoluene, alpha-methylstyrene, N,N-dimethyl acrylamide, N-t-butyl acrylamide, N-vinyl pyrrolidone, and acrylonitrile.

7. The seawater erodible terpolymer of claim 1 wherein said polymer has a molecular weight in the range from 1,000 to 200,000 g/mol.

8. A terpolymer comprising the reaction product of monomer A, where A comprises
    a) one or more triarylsilyl(meth)acrylates (XSiR$_3$) wherein each R may be the same or different and is a substituted or unsubstituted aryl or heteroaryl group, X is the residue of an acryloxy or methacryloxy group, with one or more ethylenically unsaturated monomers of group B wherein B represents methyl methacrylate and one or more other different ethylenically unsaturated monomers copolymerizable with A, in the presence of a polymerization catalyst or initiator and characterized by residue of monomer A in said polymer of above 9 to less than 20 mole percent of the copolymer, and wherein the copolymer is characterized by an Erosion Rate in sea water of from 2 to 15 microns per month; and
    b) one or more stabilizing agent(s) selected from a dehydrating agent, a zeolite, an acid neutralizer, an amino containing compound, an antioxidant, a chelator, and/or an alkoxy silane.

9. The terpolymer of claim 8 where at least one R is selected from unsubstituted aryl, phenyl, aryl substituted by one or more chlorine, fluorine, bromine, iodine, alkyl, perfluoroalkyl, napthyl, fluorenyl, anthracenyl, phenanthrenyl, pyrenyl, alkylether, substituted alkylether, arylether, substituted arylether; amino substituted group or mixtures thereof and the polymer is characterized by an Erosion Rate of from 2 to 15 microns per month.

10. The terpolymer of claim 8 wherein monomer A is triphenylsilyl acrylate or triphenysilyl methacrylate.

11. The terpolymer of claim 8 wherein said polymer has a molecular weight in the range from 1,000 to 200,000 g/mol.

12. A terpolymer composition comprising the polymer of claim 1 and an organic solvent.

13. A terpolymer composition comprising the polymer of claim 8 and an organic solvent.

14. The terpolymer composition of claim 13 further comprising a stabilizing agent selected from a dehydrating agent, a zeolite, an acid neutralizer, an amino containing compound, an antioxidant, a chelator, and an alkoxy silane.

15. A self-polishing marine antifouling coating composition comprising the terpolymer of claim 1, a toxicant, and a stabilizing agent, and characterized by an Erosion Rate in seawater of about 2 to 15 microns per month.

16. The self-polishing marine antifouling coating composition of claim 15 wherein said stabilizing agent is present in said composition from 0.1 to 10 weight percent based upon the weight of said composition.

17. The self polishing antifouling coating composition of claim 15, further comprising rosin and rosin derivatives.

18. The self polishing antifouling coating composition of claim 17 in which the rosin and rosin derivatives are present in the range of 5 to 60 weight percent of the terpolymer.

19. A self-polishing antifouling coating composition for fresh water or brackish water applications comprising the terpolymer of claim 1, a toxicant, and a stabilizing agent, and characterized by an Erosion Rate of about 2 to 15 microns per month in the fresh water or brackish water of the application.

* * * * *